(12) United States Patent
Chapples et al.

(10) Patent No.: US 8,741,120 B2
(45) Date of Patent: Jun. 3, 2014

(54) HUMIDITY CONTROL APPARATUS FOR ELECTROCHEMICAL SENSORS

(75) Inventors: John Chapples, Poole (GB); Martin Willett, Waterlooville (GB)

(73) Assignee: Life Safety Distribution AG, Uster (CH)

( * ) Notice: Subject to any disclaimer, the term of this patent is extended or adjusted under 35 U.S.C. 154(b) by 1412 days.

(21) Appl. No.: 11/872,392

(22) Filed: Oct. 15, 2007

(65) Prior Publication Data

US 2009/0095640 A1    Apr. 16, 2009

(51) Int. Cl.
*G01N 27/407*  (2006.01)
*G01N 27/406*  (2006.01)

(52) U.S. Cl.
CPC .......... *G01N 27/406* (2013.01); *G01N 27/4067* (2013.01)
USPC ........... 204/430; 204/424; 204/426; 236/44 R

(58) Field of Classification Search
CPC  G01N 27/406; G01N 27/4067; G01N 27/304
USPC ................ 236/9, 44 R; 261/142; 128/203.27; 204/421–429
See application file for complete search history.

(56) References Cited

U.S. PATENT DOCUMENTS

| 4,265,714 | A | * | 5/1981 | Nolan et al. ................ 205/779.5 |
| 4,723,439 | A | * | 2/1988 | Asakura et al. .............. 73/29.05 |
| 4,921,642 | A | * | 5/1990 | LaTorraca ..................... 261/142 |
| 4,998,431 | A | * | 3/1991 | Jappinen et al. ............... 73/1.04 |
| 5,644,080 | A | * | 7/1997 | Stormbom et al. ........ 73/335.05 |
| 2007/0023536 | A1 | * | 2/2007 | Baston ........................ 236/44 C |

FOREIGN PATENT DOCUMENTS

| DE | 39 33 727 A1 | 5/1990 |
| GB | 1 296 156 | 11/1972 |
| JP | 53-45242 | 4/1978 |
| JP | 2005-214685 | 8/2005 |

OTHER PUBLICATIONS

Data supplied by Espacenet's database indicating that English translation of abstract of DE 3933727 (A1) is not available, May 1990.
English translation of abstract of JP 53045242, May 1978.
English translation of abstract of JP 2005214685, Aug. 2005.
Extended European Search Report corresponding to Application No. EP 08 16 6531, dated Dec. 7, 2009.

* cited by examiner

*Primary Examiner* — Keith Hendricks
*Assistant Examiner* — Kourtney S Carlson
(74) *Attorney, Agent, or Firm* — Husch Blackwell LLP

(57) ABSTRACT

Devices and methods are disclosed that can adjust a hydration level in an electrochemical sensor or an instrument which includes such a sensor. The device can include a chamber which can, at least in part, surround an inflow port of the sensor. An adjacent reservoir of water can provide a source of water vapor which can be infused into the sensor.

21 Claims, 2 Drawing Sheets

HUMIDITY CONTROL APPARATUS FOR ELECTROCHEMICAL SENSORS

FIELD

The invention pertains to electrochemical gas sensors. More particularly, the invention pertains to devices and methods to adjust levels of hydration in such sensors subsequent to exposure to an ambient environment.

BACKGROUND

Electrochemical gas sensors of the type that are commonly used in portable and fixed instrumentation are frequently employed in diverse and sometimes extreme operating environments. Most sensors would be expected to function continuously at temperatures between −20 degrees C. to 40 degrees C. and 15% to 85% ambient humidity, and intermittently at even more extreme conditions.

Operating electrochemical cells at the extremes of the their respective operating range for extended periods of time can lead to performance degradation as the internal electrolyte composition responds to the external environmental conditions. For example such cells may lose or gain water in response to their respective working environments.

The recent trends towards smaller cell package size means that cell performance is even more susceptible to extremes of environmental conditions. Under continued operation this might result in significant degradation in cell performance or even failure.

There thus continues to be a need for systems and methods which support gas sensor operability at or in extreme external environmental conditions. Preferably, such enhanced operability could be provided relative to known types of electrochemical gas sensors.

DETAILED DESCRIPTION

Figure 1:
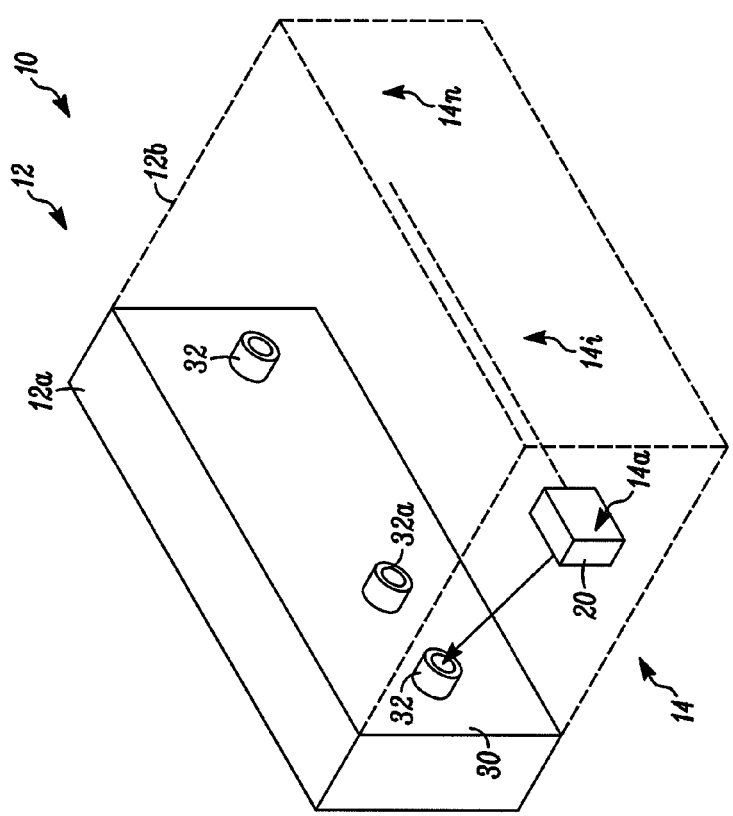
FIG. 1 is a block diagram of a system in accordance with the invention.

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

Applicant has recognized that there is a need to be able to modify hydration of electrochemical-type sensors. Modification can take place, in accordance with the invention via various exemplary processes. An assumption as to the environmental history of usage a sensor can be made and that sensor can be exposed to a controlled RH environment that is deemed appropriate for the respective history. Alternately, a measurement can be made of one or more parameters which indicate the state of humidity of the sensor, and the sensor can then be exposed to an appropriate RH environment. Multiple measurements could of course be made during the course of exposure to the environment. In yet another alternate, information can be collected during operation of the sensor to subsequently determine the appropriate remedial RH environment.

In accordance with the invention electrochemical gas sensors can be hydrated or dehydrated after use to adjust the sensor's electrolyte concentration to a predetermined range. This process can be conveniently carried out when the respective sensor, or associated detector is receiving routine service or battery charging. In this regard, those of skill will understand that either the entire detector or the sensor element alone could be exposed to a hydrating/dehydrating environment.

Electrolyte adjustment can be implemented by exposing the sensor to water vapor, to moving streams of mixed wet or dry air, exposing the sensor to solid dryers or any other way which provides the desired hydration or dehydration.

Effective electrolyte adjustment can include adjusting the electrolyte to its allowable operable range. Those of skill in the art will recognize that it is not necessary to readjust the respective sensor to its original, out the factory door condition, in view of that fact that electrolytes for such sensors are usually chosen partly on the basis that they continue to function adequately across as wide a range as possible. In addition, where cells have been exposed to a common environment, an open loop hydrating/dehydrating methodology could be developed which could be applied to a plurality of cells which have been exposed to the common environment.

In a preferred method of practicing the invention, an electrochemical gas sensor component within a gas detector is hydrated, or dehydrated, through modification of the local humidity external to the sensor, while the detector, or, instrument is not in use. For example, hydration, or dehydration, could take place while the batteries of the detector are being re-charged. In accordance herewith, the present method would replenish or extract an equivalent amount of water vapor to that lost/gained by the sensor during a period of operation, thereby significantly reducing or eliminating environmental effects on sensor performance.

In one aspect, the detector can be placed in a sealed chamber in which the local humidity is modified/controlled in a fixed or dynamic fashion so as to restore the electrolyte concentration within the sensor to the manufacturer's intended composition. The relative humidity, RH of the modified instrument environment may be static and set at an appropriate level to compensate for the working conditions of the instrument/cell, or the modified RH environment may be dynamic and capable of being changed or controlled to an optimum level.

The optimum level may be determined by measurement of a physical characteristic of the cell that varies with degree of hydration of the electrolyte. For example, pH of the electrolyte could be measured as an indicator of hydration.

In a disclosed embodiment, a shroud/jacket can provide an interface with a detector's front panel to provide a seal against the external environment. The seal can be maintained with respect to the detector, or sensor element, using a variety of different types of seals such as O-rings, a gasket material, or a molded rubber insert.

The jacket can contain a salt solution, water or other hydrating solution, whose temperature is/can be controlled via a heater element. The jacket can also include a vapor permeable membrane through which moisture vapor can pass into an air space enclosed between the instrument sensor and the shroud. Suitable materials for the membrane material include micro-porous polymers such as PTFE or polyethylene. The shroud containing the solution could include an aperture to enable replenishment of lost water.

In accordance with the above, various embodiments include:

I) Configuring the shroud/Jacket so that it will totally enclose the instrument.

II) Using the shroud to enclose multiple instruments.

III) Providing a saturated salt solution in the shroud.

IV) Providing an unsaturated solution in the shroud.

V) The shroud can contain a salt solution with an RH between 5 and 95% RH that is non-temperature controlled. Preferably, the imposed RH would be in the range 40 to 60% to match that of the original electrolyte solution within the cell. However, the RH of the shroud could be chosen and adjusted to compensate for the local working environment. For example. If the cells have been operating in a dry warm environment then a shroud might be chosen to provide a high RH environment to compensate for higher than average loss of water vapor from the cell and vice versa.

VI) The applied RH % may be controlled by varying the temperature of the salt solution via a heater element.

VII) The temperature and applied humidity might be specifically controlled and adjusted to an optimum level by measuring a characteristic of the cell that varies with degree of electrolyte hydration. Examples include electrolyte pH, cell capacitance, impedance, or noise. Alternately, cell response to an applied current or voltage pulse can be sensed.

VIII) The local RH environment of the instrument/cell could be modified remotely, provided the instrument is in an enclosed chamber. In addition to the above, other suitable methods might be to blend two air streams of differing humidity to a single flow of a specific humidity.

FIG. 1 illustrates an apparatus 10 which embodies the invention. A hydrating housing 12 can partially, via section 12a, or fully, as illustrated by expansion section 12b (in phantom), provide a hydrating/dehydrating environment for a plurality of electrochemical gas detectors 14, having members 14a, 14b . . . 14n. Electrolyte adjustment can take place while a battery of the respective detector, such as detector 14i is being recharged.

Figure 2:
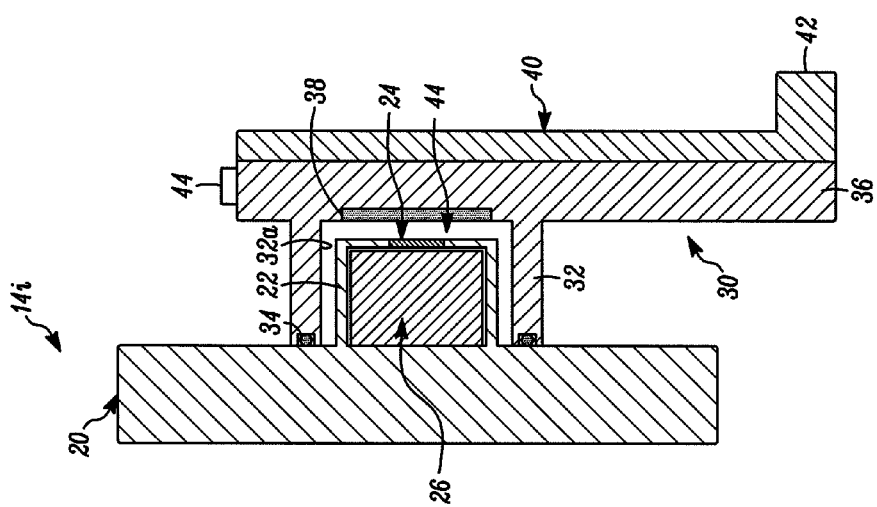
FIG. 2 is an enlarged diagram illustrating additional aspects of the invention.

In FIG. 2 detector 14i is illustrated positioned adjacent to section 12a to be hydrated. Detector 14i includes, for example, a sensor component 20 having a cylindrically extending portion 22 with an environmental access aperture 24.

An electrochemical sensing element 26 is carried within the portion 22 exposed to the environment via aperture 24. Those of skill will understand that the detector 14i will also include other conventional elements which need not be illustrated here.

Apparatus 12a includes a housing section 30 with a cylindrical, hollow, protruding member, or jacket, 32. Member 32 has an interior peripheral surface 32a, and also carries a seal 34, for example an O ring or other type of seal such as a gasket or molded insert.

When detector 14i is positioned against the seal 34, the external environment is excluded and the electrolyte of the sensor element 26 can be adjusted by apparatus 12a.

The jacket 32 contains, for example, a salt solution 36 whose temperature is/can be controlled via a heater element 40. The heater element 40 can be energized from an exterior source via a connector 42. It will be understood that other solutions could be used to carry out a hydrating or dehydrating process.

The apparatus 12a also contains a vapor permeable membrane 38 through which moisture vapor can pass into an air space 44 sandwiched between the sensor element 26 and the jacket 32. Suitable materials for the membrane's material include micro-porous polymers such as PTFE or polyethylene. The apparatus 12a containing the salt solution 36 has an aperture 44 usable to replace lost water.

Once a suitable period of time has elapsed, detector 14i can be removed from apparatus 12a and placed back into service. On removal, the sensor element 26 should exhibit improved operational characteristics.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. A humidity control apparatus comprising:
a gas detector with a front panel and an electrochemical sensor containing an electrolyte of a first hydration level,
the front panel having a cylindrically extending portion, the electrochemical sensor is carried within the cylindrically extending portion;
a housing with a protruding member which defines, at least in part, an interior region and, a second closed region, the detector positioned with the cylindrically extending portion and electrochemical sensor extending into the interior region of the housing which in part surrounds an inflow port of the gas detector, the detector's front panel and protruding member providing a seal against the external environment;
a vapor permeable membrane between at least a portion of the two regions;
a salt solution carried within the second region; and a heating element carried adjacent to the second region that operates to carry out one of hydrating and dehydrating of the electrolyte of the electrochemical sensor, wherein the detector's front panel and the protruding member form a sealed chamber around the two regions in which a relative humidity is controlled in a fixed or dynamic fashion so as to restore a concentration of the electrolyte within the electrochemical sensor to the first hydration level and wherein a relative humidity in the sealed chamber is controlled by varying the temperature of the salt solution via the heating element.

2. An apparatus as in claim 1 where portions of the interior region carry an externally accessible deformable seal.

3. An apparatus as in claim 1 where the housing includes a side wall that, at least in part, bounds the interior region.

4. An apparatus as in claim 3 where the side wall includes a peripheral surface, adjacent to part of the interior region, the peripheral surface having a closed cross-section.

5. An apparatus as in claim 4 where the closed cross-section is one of at least partly curved, or, partly linear.

6. An apparatus as in claim 5 where the membrane is oriented so as to be substantially parallel to a plane that includes the cross-section.

7. An apparatus as in claim 5 where the side wall extends generally parallel to a line normal to at least a portion of the membrane.

8. An apparatus as in claim 7 where the side wall has first and second ends with one end terminating adjacent to the membrane, and the other displaced therefrom in a direction along the line normal thereto.

9. An apparatus as in claim 8 which includes at least one of an electrical connector for the heating element, and, a fill port for the second region.

10. An apparatus as in claim 9 where the interior region of the housing substantially encloses a selected gas detecting member.

11. An apparatus as in claim 1 wherein the housing further comprises a jacket containing a hydrating solution.

12. An apparatus comprising:
a gas detector with a front panel and an electrochemical sensor containing an electrolyte of a first hydration level carried by the front panel;
a jacket containing a hydrating solution the jacket having a protruding member which surrounds an inflow port of the gas detector, the protruding member defines, at least in part, an interior region and, a second closed region containing the hydrating solution, the detector positioned with an environmental access aperture of the electrochemical sensor extending into the interior region of the jacket which in part surrounds an inflow port of the gas detector, the detector's front panel and protruding member providing a seal against the external environment wherein the detector's front panel and the jacket form a sealed chamber around the interior region and second closed region;
a vapor permeable membrane between at least a portion of the two regions; and
a heating element carried adjacent to the second region that operates to carry out one of hydrating and dehydrating of the electrolyte of the electrochemical sensor wherein a relative humidity within the sealed chamber is controlled in a fixed or dynamic fashion so as to restore a concentration of the electrolyte within the gas sensor to the first hydration level and wherein a relative humidity in the sealed chamber is controlled by varying the temperature of the hydrating solution via the heating element.

13. An apparatus as in claim 12 where portions of the interior region carry an externally accessible deformable seal.

14. An apparatus as in claim 12 where the housing includes a side wall that, at least in part, bounds the interior region.

15. An apparatus as in claim 14 where the side wall includes a peripheral surface, adjacent to part of the interior region, the peripheral surface having a closed cross-section.

16. An apparatus as in claim 15 where the closed cross-section is one of at least partly curved, or, partly linear.

17. An apparatus as in claim 16 where the membrane is oriented so as to be substantially parallel to a plane that includes the cross-section.

18. An apparatus as in claim 16 where the side wall extends generally parallel to a line normal to at least a portion of the membrane.

19. An apparatus as in claim 18 where the side wall has first and second ends with one end terminating adjacent to the membrane, and the other displaced therefrom in a direction along the line normal thereto.

20. An apparatus as in claim 19 which includes at least one of an electrical connector for the heating element, and, a fill port for the second region.

21. An apparatus as in claim 20 where the interior region of the housing substantially encloses a selected gas detecting member.

* * * * *